(12) United States Patent
Johansen et al.

(10) Patent No.: US 6,951,554 B2
(45) Date of Patent: Oct. 4, 2005

(54) DEFLECTING CATHETER

(75) Inventors: Jerald A. Johansen, Canyon Lake, CA (US); Carl E. Yee, San Diego, CA (US); John M. Neet, Lawrence, KS (US)

(73) Assignee: Intraluminal Therapeutics Inc., Kansas City, KS (US)

( * ) Notice: Subject to any disclaimer, the term of this patent is extended or adjusted under 35 U.S.C. 154(b) by 159 days.

(21) Appl. No.: 10/248,071

(22) Filed: Dec. 16, 2002

(65) Prior Publication Data

US 2004/0116851 A1 Jun. 17, 2004

(51) Int. Cl.[7] .............................................. A61M 31/00
(52) U.S. Cl. ................. 604/509; 604/524; 604/102.02; 604/103.04; 604/103.05; 604/103.07; 604/103.1; 604/95.04; 604/915; 606/194; 600/434; 600/435
(58) Field of Search .................. 600/433–435; 604/264, 523–529, 533, 544, 915–917, 920, 500, 507–510, 96.01, 97.01, 101.01, 101.02, 102.01, 102.02, 103.04, 103.05, 103.07, 103.09, 103.1, 95.04, 95.01, 95.03; 606/192, 194

(56) References Cited

U.S. PATENT DOCUMENTS

| | | |
|---|---|---|
| 3,773,034 A | 11/1973 | Burns et al. |
| 4,906,230 A | 3/1990 | Maloney et al. |
| 4,909,787 A | 3/1990 | Danforth |
| 5,061,273 A | 10/1991 | Yock |
| 5,269,757 A * | 12/1993 | Fagan et al. ............. 604/95.01 |
| 5,498,239 A | 3/1996 | Galel et al. |
| 5,619,993 A | 4/1997 | Lee |
| 5,711,754 A * | 1/1998 | Miyata et al. ................ 600/18 |
| 5,807,249 A | 9/1998 | Qin et al. |
| 5,814,016 A * | 9/1998 | Valley et al. ............ 604/96.01 |
| 5,951,482 A | 9/1999 | Winston et al. |
| 6,013,072 A | 1/2000 | Winston et al. |
| 6,027,462 A | 2/2000 | Greene et al. |
| 6,048,349 A | 4/2000 | Winston et al. |
| 6,059,739 A | 5/2000 | Baumann |
| 6,063,093 A | 5/2000 | Winston et al. |
| RE36,764 E * | 7/2000 | Zacca et al. ................ 606/159 |
| 6,159,227 A * | 12/2000 | Di Caprio et al. .......... 606/192 |
| 6,165,123 A | 12/2000 | Thompson |
| 6,203,558 B1 * | 3/2001 | Dusbabek et al. .......... 606/198 |
| 6,217,527 B1 | 4/2001 | Selmon et al. |
| 6,221,049 B1 | 4/2001 | Selmon et al. |
| 6,231,546 B1 | 5/2001 | Milo et al. |
| 6,235,000 B1 | 5/2001 | Milo et al. |
| 6,394,976 B1 | 5/2002 | Winston et al. |
| 6,406,442 B1 | 6/2002 | McFann et al. |
| 6,463,313 B1 | 10/2002 | Winston et al. |
| 2001/0000041 A1 | 3/2001 | Selmon et al. |
| 2001/0012924 A1 | 8/2001 | Milo et al. |
| 2002/0032391 A1 | 3/2002 | McFann et al. |

* cited by examiner

Primary Examiner—Cris L. Rodriguez
(74) Attorney, Agent, or Firm—Armstrong Teasdale LLP (57) ABSTRACT

A catheter includes a distal end, a proximal end, an outer tube extending from the distal end to the proximal end, and an inner tube extending through the outer tube. The distal end including a corrugated section attached to an end of the inner tube and an asymmetric balloon attached to the outer tube and configured to deflect the distal end of the catheter.

32 Claims, 5 Drawing Sheets

DEFLECTING CATHETER

BACKGROUND OF INVENTION

This invention relates generally to catheters, and more specifically to steerable catheters.

Guide wires are routinely steered through the human vascular system and, with operator experience, can be steered through vascular obstructions and occlusions. Catheters provide support to the guide wire and assist with directing a guide wire in the vessel. Changing the distal tip position of a catheter allows easier travel through tortuous paths by changing the direction of the path while in the body. Guide catheters, for example, are used to canulate the ostium of a coronary artery to facilitate angiographic examinations and interventions. Other catheters, such as balloon catheters or support catheters are introduced through the guide catheter to travel within the coronary arteries to more distal locations. These catheters are typically used in combination with a guide wire.

SUMMARY OF INVENTION

In one aspect, a catheter is provided that includes a distal end, a proximal end, an outer tube extending from the distal end to the proximal end, and an inner tube extending through a length of the outer tube. The proximal end comprising an inflation port, an inner hub bonded to the outer tube and forming a seal therewith, and a flexible tube extending between the inflation port and the inner hub. The outer tube and the inner hub configured to rotate with respect to the inflation port.

In another aspect, a catheter is provided that includes a distal end, a proximal end, an outer tube extending from the distal end to the proximal end, and an inner tube extending through the outer tube. The distal end including a corrugated section attached to an end of the inner tube and an asymmetric balloon attached to the outer tube and configured to deflect the distal end of the catheter.

In another aspect, a method is provided for deflecting a catheter. The catheter includes a distal end, a proximal end, an outer tube extending from the distal end to the proximal end, and an inner tube extending through the outer tube. The proximal end includes an inflation port and a rotating hub is bonded to the outer shaft. A flexible tube extends between the inflation port and the rotating hub and the outer tube and inner tube are rotatable with respect to the inflation port. The distal end includes a corrugated section attached to an end of the inner passage tube and a deflection balloon attached to the outer tube and configured to expand more on one side than another side. The method comprising providing a fluid at the inflation port, pressurizing the fluid such that it passes through the inflation port, through the flexible tube, into the rotating hub, into a space between the inner tube and the outer tube, and into the deflecting balloon, and causing the balloon to inflate until a desired deflection of the distal end is achieved.

DETAILED DESCRIPTION

A low profile, deflectable catheter includes an asymmetric balloon that deflects a distal tip of the catheter in situ. The catheter is one of an over-the-wire configuration in which a guide wire is introduced into a proximal end of the catheter and exits a distal end, and a rapid exchange configuration in which the guide wire enters the catheter near the distal end and exits the catheter at the distal end. In either configuration, the catheter is advanced along the guide wire until the distal end of the catheter is near the distal end of the guide wire. When the catheter is appropriately positioned, pressurization of the asymmetric balloon forms an arc that deflects the catheter and guide wire from their present path.

Figure 1:
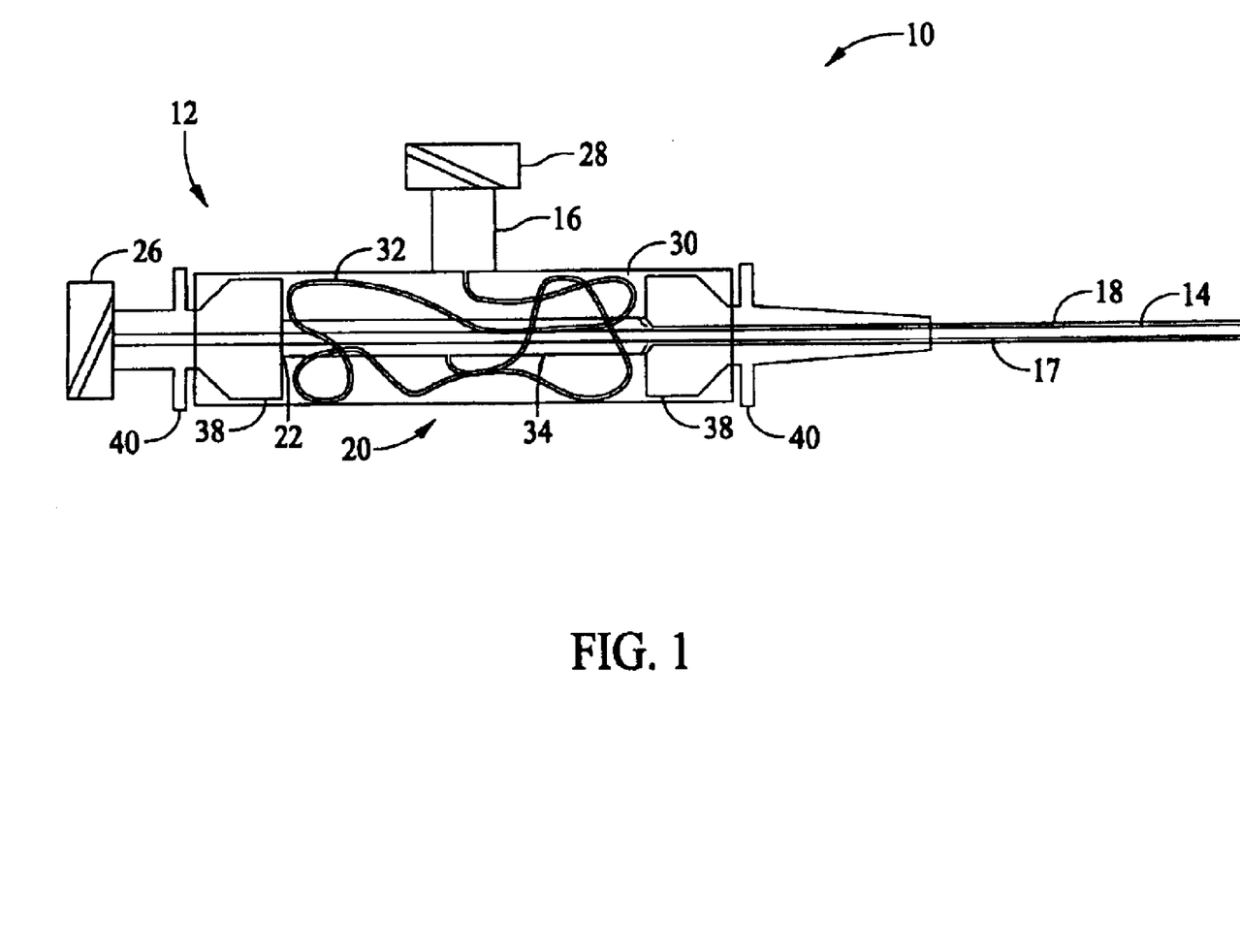
FIG. 1 illustrates a proximal end of a deflecting catheter in accordance with one embodiment of the present invention.

FIG. 1 illustrates a proximal portion of a deflecting catheter 10 including a proximal end 12. Catheter 10 includes an inner tube 14 through which a guide wire (not shown) is passed from proximal end 12 to a distal end (not shown in FIG. 1) of catheter 10. An inner diameter of inner tube 14 is slightly larger than the guide wire to be used. For example, if a 0.014 inch diameter coronary guide wire is utilized, a typical inner diameter of inner tube 14 is from approximately 0.017 inch to approximately 0.020 inch. Typical dimensions are used herein for a catheter utilized with 0.014 inch diameter coronary guide wires. Other embodiments of catheter 10 exist, including, but not limited to, a catheter utilizing a 0.010 inch diameter neuro wire, a 0.035 inch diameter peripheral wire, or any other diameter guide wire. Such embodiments are fabricated by scaling inner tube 14 and other catheter components described herein below.

Proximal end 12 includes an inflation port 16 in fluid communication with a passageway 17 extending through an outer tube 18. Inflation port 16 is attached to a rotating hub system 20 that is bonded to bonding point 22 which is connected to a proximal end of tube 18 and forms a seal therewith. In one embodiment, the bond at bonding point 22 is formed with a light-activated adhesive or any suitable adhesive. Inner tube 14 extends through outer tube 18 and forms passageway 17 therebetween. In one embodiment, proximal end 12 of catheter 10 is configured to allow inflation port 16 to remain stationary while outer tube 18 of catheter 10 is rotated to change an orientation of a distal end of catheter 10, as further described below.

Inner tube 14 extends to a LUER fitting 26 and is bonded therewith to form a continuous guide wire lumen from proximal end 12 to distal end (not shown in FIG. 1) of catheter 10. When using catheter 10, the guide wire may be removed and fluids, for example, one or more of contrast media, drugs, and other solutions can be injected through LUER fitting 26. The fluids are delivered through inner tube 14 to a proximal end (not shown in FIG. 1) of catheter 10.

In one embodiment, proximal end 12 also includes a second LUER fitting 28 and an outer hub 30 attached to inflation port 16. Second LUER fitting 28 is configured to attach to an inflation device. Hub system 20 also includes a flexible tube 32 and an inner hub 34. Flexible tube 32 is fluidly connected to inflation port 16 and to inner hub 34 which extends from a proximal end of outer tube 18. Flexible tube 32 provides a fluid conduit between LUER fitting 28 and passageway 17. Fluid is injected into inflation port 16 through LUER fitting 28 and flows through flexible tube 32 to passageway 17. The fluid then flows to a distal portion of catheter 10 and into a deflecting balloon (not shown in FIG. 1) to deflect the distal end (not shown in FIG. 1) of catheter 10.

Rotating hub system 20 further includes bushings 38 within outer hub 30 that rotate upon and center inner hub 34. Components within rotating hub system 20 are constrained axially with an end piece 40 that is also rotatable with respect to outer hub 30. In at least one use, outer hub 30 and inflation port 16 are held in a relatively stationary position while LUER fitting 26 is rotated. Rotation of LUER fitting 26 causes a rotation of at least end pieces 40, bushings 38, inner hub 34, and outer tube 18 with respect to outer hub 30 and inflation port 16.

In one embodiment, inner tube 14 is a three-layer tube. An inner layer of tube 14 is fabricated from polyimide, polytetrafluoroethylene (PTFE) or similar lubricious material that allows a guide wire to be readily advanced or retracted through inner tube 14 without any appreciable friction, especially as catheter 10 conforms to a tortuous path. In one embodiment, the inner layer is approximately from 0.0005 inch to approximately 0.001 inch thick. A middle layer of inner tube 14 is a coil (not shown) configured to maintain a passageway through tube 14 in a substantially round configuration, even when catheter 10 follows a tortuous intraluminal path. The coil reduces the likelihood of pinching the guide wire so that the guide wire will move freely through tube 14. In one embodiment, the coil is constructed of flat stainless steel ribbon. The flat ribbon construction minimizes a thickness of the middle layer to keep a low profile for tube 14. In a particular embodiment, the coil is constructed from 0.0005 inch×0.0025 inch type 304 stainless steel ribbon with 110 winds per inch. A third, outer layer of inner passage tube 14, in one embodiment, is fabricated from polyimide or PTFE and strengthens tubs 14 against hydraulic pressure during inflation of a balloon at distal end of catheter 10, as described below. Typically, this outer layer is approximately from 0.0005 inch to about 0.001 inch thick.

An overall length of inner tube 14 is from approximately 40 cm to approximately 150 cm. The length depends on the length of the catheter needed for a particular anatomy that is being catheterized through utilization of catheter 10. Other tubing materials are available and can be utilized for inner tube 14. For example, composite materials exist that maintain their shape and provide sufficient strength. In an alternative embodiment, polyetheretherketone (PEEK) is used to fabricate the first and/or third layers. In further embodiments, coils constructed from other types of steels or metals are used for the middle layer of tube 14.

Figure 2:
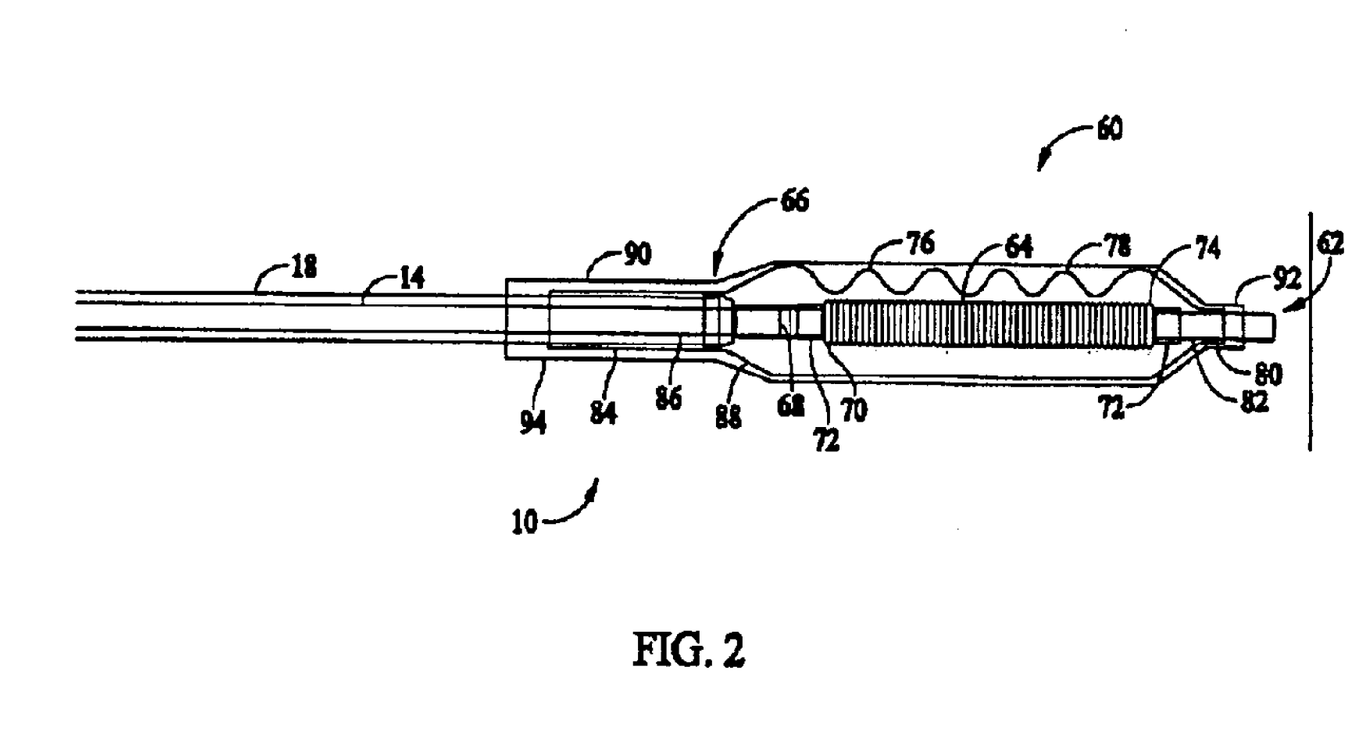
FIG. 2 illustrates a distal end of the deflecting catheter shown in FIG. 1.

FIG. 2 is a distal end 60 of catheter 10 including a tip 62 and a corrugated section 64 that provides flexibility to distal end 60 and enables distal tip 62 to deflect. Corrugated section 64 allows maneuvering of distal tip 62 to a region where deflection is desired. While corrugated section 64 is shown at distal end 60 of catheter 10 in the illustrated embodiment, in alternative embodiments, corrugated section 64 and a deflection point of catheter 10 are positioned at various locations along the length of catheter 10 by splicing corrugated section 64 into inner tube 14.

Corrugated section 64 is a section of tubing that is more flexible than inner tube 14 and that allows a user to maintain an open lumen for a guide wire (not shown) when section 64 is bent. In one embodiment, corrugated section 64 is fabricated from a thin material which allows catheter 10 to maintain a low profile and withstand pressurization up to at least about 20 atmospheres. In an exemplary embodiment, corrugated section 64 is constructed of corrugated polyethylene terephthalate (PET) heat shrink tubing with a wall thickness of approximately 0.0005 inch. Corrugated section 64 is constructed by placing a section of tubing with an inner diameter of approximately 0.024 inch over a 0.019 inch diameter PTFE coated mandrel. The PET tubing is heated to approximately 300 degrees F. which causes the tube to contract to the mandrel diameter. The corrugations are formed by compressing the tubing axially causing the material to buckle in tightly spaced intervals. The corrugations are thermally set by raising the temperature to approximately 374 degrees F. allowing the corrugated tube to contract further and tightening the spacing of the corrugations. The material is then cooled to ambient temperature and the mandrel is removed. The thermal set establishes a memory for corrugated section 64 so that it straightens after having been bent or deflected. In one embodiment, corrugated section 64 is attached to a distal end 66 of inner tube 14 forming a continuous lumen and providing a path for the guide wire.

To construct distal end 60 of catheter 10, a protective sleeve 68 is placed over an end of inner tube 14 to prevent the above described middle layer of inner passage tube 14 from damaging corrugated section 64. In one embodiment, protective sleeve 68 is a PET heat shrink tubing having a length of approximately 0.040 to 0.080 inch. The tubing extends approximately half way onto inner tube 14 and the remainder of sleeve 68 extends beyond end 66 of inner tube 14. In one embodiment (not shown), a mandrel is inserted through protective sleeve 68 and into inner tube 14 to maintain the continuity of the lumen extending through inner tube 14. Heat is applied to protective sleeve 68 to shrink it onto inner tube 14 and cover the exposed middle layer.

A proximal end 70 of corrugated section 64 extends over inner tube 14 and protective sleeve 68 and, in one embodiment, is shrunk onto inner tube 14 by applying heat. In other embodiments, corrugated section 64 is bonded to inner tube 14 by applying ultraviolet, light curable, or a cyanoacrylate adhesive.

Distal end 60 includes a pair of radiopaque marker bands 72 attached to corrugated section 64. A first band 72 is attached to proximal end 70 and a second band 72 is attached to distal end 74 to allow a deflection zone to be identified under fluoroscopy during a catherization procedure. In other embodiments, bands 72 are fabricated from gold and/or platinum foils that can be crimped onto corrugated section 64 and bonded with a light activated or a cyanoacrylate adhesive. Alternatively, bands 72 are attached to non-corrugated ends of the corrugated tubing to minimize a profile of catheter 10.

Inner tuber 14 extends within a length of outer tube 18 and provides a fluid path between hub system 20 and deflection balloon 76. In one embodiment, an inner diameter of outer tube 18 is approximately 0.004 inch larger than an outer diameter of inner tube 14. Outer tube 18 is constructed to withstand an inflation pressure of deflection balloon 76 and transmit rotational displacement (e.g. torque) from proximal end 12 to distal end 60 so that a deflection orientation can be changed during use of catheter 10. Deflection balloon 76, when inflated, achieves a curved orientation based upon a "memory" of the balloon material as described below. Distal end 62 of catheter 10 is deflected at a location of deflection balloon 76.

In one embodiment, outer tube 18 is a three-layered tube similar to inner tube 14. Outer tube 18 includes an inner layer fabricated from polyimide approximately 0.0005 inch to 0.005 inch thick. A middle layer is fabricated from braided stainless steel wire. The wire is 0.0005 inch×0.0025 inch flat type 304 stainless steel wire with approximately 100–130 PIC (crossings per inch). The middle layer provides reinforcement and transmits torque from proximal end 12 to distal end 60. An outer layer is fabricated from polyurethane and fills the voids within the braiding to form a smooth, atraumatic surface. In one embodiment, the outer layer is approximately 0.0005 inch thick to about 0.001 inch thick. In other embodiments, other tubular constructions are utilized.

In one embodiment, deflection balloon 76 is formed from 0.038 inch PET heat shrink tubing having an approximate 0.00025 inch wall thickness. The tubing is pressurized with air to approximately 40 psi and then the tubing is curved around a 0.159 inch cylinder that is heated to approximately 370 degrees F. Deflection balloon 76 is then cooled to an ambient temperature. When cooled, deflection balloon 76 has a curved configuration. Cooled balloon 76 can be straightened and when straightened, a longer arc side of deflection balloon 76 forms folds 78. Ends of deflection balloon 76 are formed by placing an appropriately sized mandrel (not shown) through deflection balloon 76 and heating the mandrel to approximately 374 degrees F. The heat allows the balloon ends to shrink around the mandrel. The ends are then trimmed to a desired length. In other embodiments, a size of deflection balloon 76 is changed for different sizes of catheters. In alternative embodiments, other materials are used to form deflection balloon 76, for example, a high-density or a low-density polyethylene.

In one embodiment, a distal end 80 of deflection balloon 76 is bonded to a distal end of inner tube 14 with at least one of ultraviolet curable adhesive, another light activated adhesive, and another adhesive type. A proximal end 84 of deflection balloon 76 is attached to a distal end 86 of outer shaft 18 by heating to approximately 290 degrees F. and applying an adhesive. In alternative embodiments (not shown), deflection balloon 76 is positioned anywhere along catheter 10 by cutting outer shaft 18 at the desired location and splicing in deflection balloon 76.

Because deflection balloon 76 is asymmetric, folds 78 develop on one side of balloon 76 when it is straightened, and the other side 88 of balloon 76 is substantially smooth. Folds 78 may result in a surface that is too rough for some catheter applications. In such a case, an alternative embodiment of catheter 10 incorporates a smoothing sleeve 90 which is placed over deflection balloon 76 to provide a smooth outer surface for distal end 60. In one embodiment, smoothing sleeve 90 is formed by blow molding a 0.012 inch inner diameter and 0.020 inch outer diameter polyether block amide (Pebax) tubing into a cylinder mold at 6 atmospheres of pressure and heated to 210 degrees F. A distal end 92 of smoothing sleeve 90 is reduced utilizing a mandrel (not shown) under tension at 250 degrees F. Distal end 92 of smoothing sleeve 90 is attached to either of corrugated section 64 (embodiment not shown) or distal end 80 of deflection balloon 76 with adhesive. A proximal end 94 of smoothing sleeve 90 is attached to proximal end 84 of deflection balloon 76 (as shown), or alternatively, to outer shaft 18 with adhesive.

Figure 3:
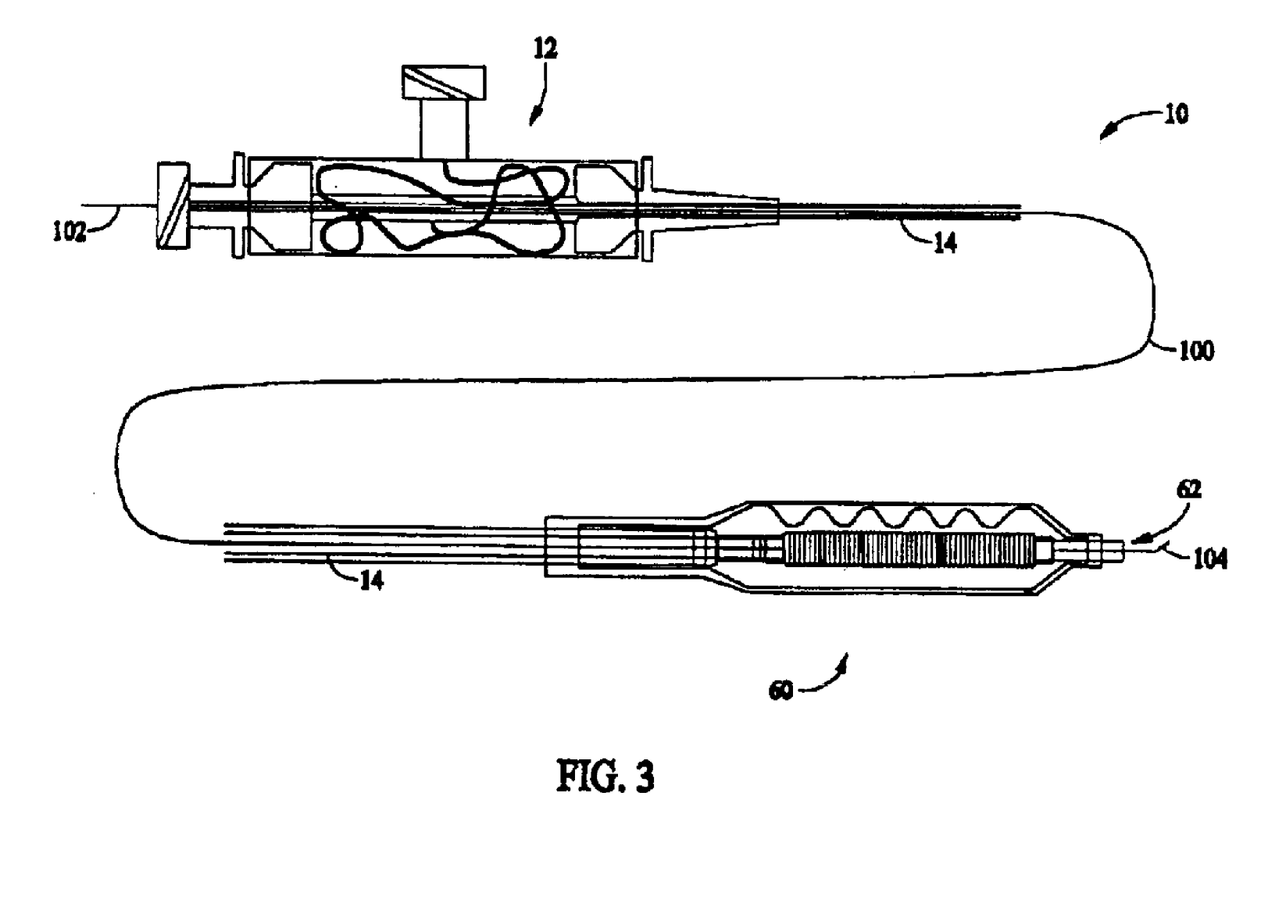
FIG. 3 is an illustration of a guide wire inserted into the catheter shown in FIGS. 1 and 2.

Referring to FIG. 3, in typical use, a guide wire 100 is inserted into inner tube 14, sometimes referred to as a guide wire lumen, of catheter 10. Insertion into inner tube 14 typically occurs either outside of the patient or after guide wire 100 has been advanced into the patient. Guide wire 100 is advanced through a vessel and guided, usually with fluoroscopy imaging and contrast injections, to the desired location. A direction of guide wire 100 is changed by rotating a proximal end 102, outside of the patient, with a resultant torque transmitted to a distal tip 104 of guide wire 100, near distal tip 62 of catheter 10. In one embodiment, distal tip 104 of guide wire 100 is angled, and rotating proximal end 102 changes an orientation of the angle and direction of guide wire 100 at its distal tip 104. When guide wire 100 can not be directed to a desired orientation, such as selecting a branch at a bifurcation, distal end 60 of catheter 10 is advanced to distal end 104 of guide wire 100.

Figure 4:
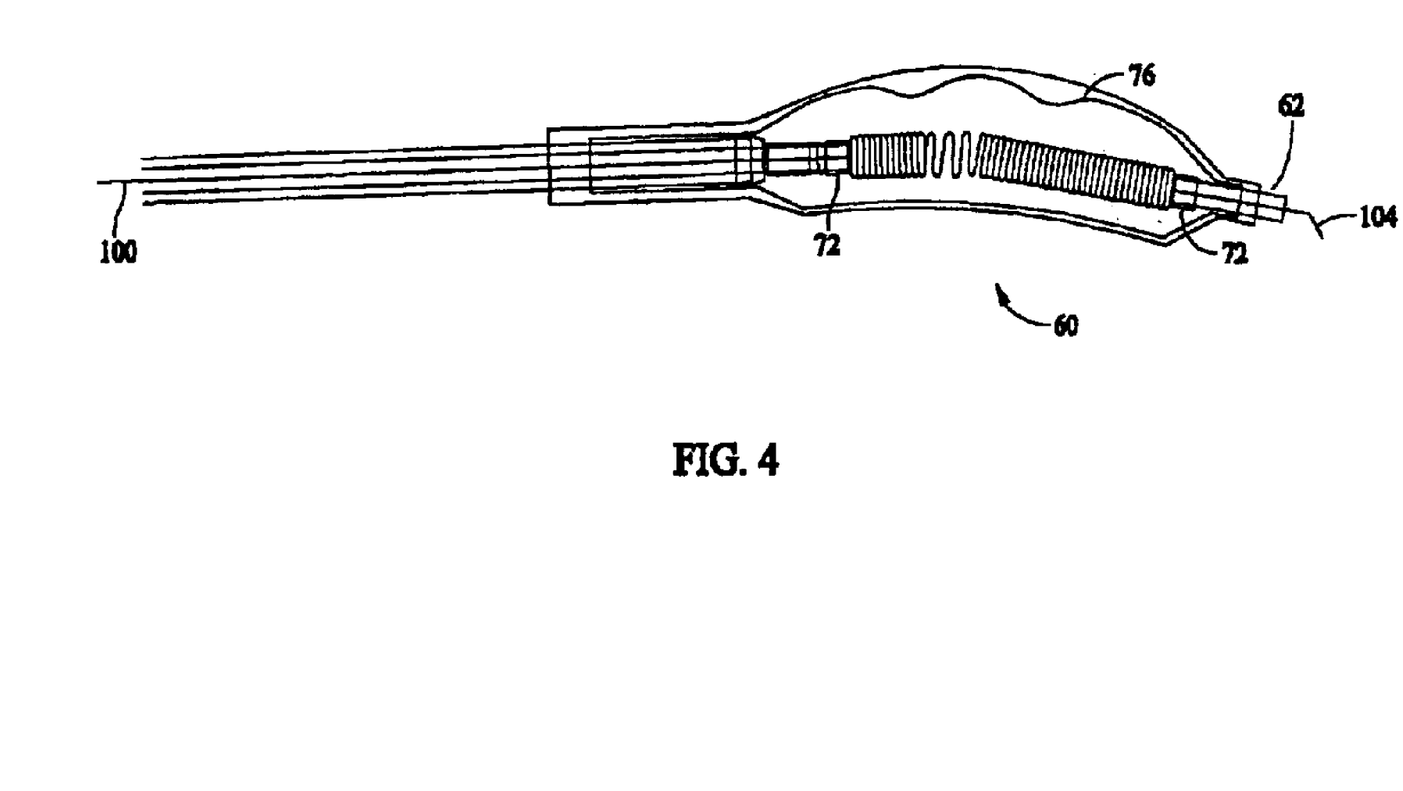
FIG. 4 is an illustration of a deflection of the distal end of the catheter shown in FIG. 2.

FIG. 4 illustrates deflecting balloon 76 of distal end 60 being pressurized. The applied pressure causes distal tip 62 to deflect as above described. An amount of deflection is proportional to the pressure within deflecting balloon 76 and the degree of deflection retained in the balloon memory. As distal tip 62 of catheter 10 is deflected, an orientation of the deflection can be determined by viewing marker bands 72 under fluoroscopy. Orientation of the deflection can be changed by rotating proximal end 12 (shown in FIGS. 1 and 3) of catheter 10 which causes distal end 62 to also rotate. The additional deflection at distal end 62 of catheter 10 helps an operator select a different path for advancing guide wire 100.

Another use of deflecting catheter 10 is to change a direction of guide wire 100 while it is being advanced through a lesion or total occlusion. Guide wire 100 is advanced through a lesion within a vessel to reach a distal portion of the vessel thereby establishing a path for therapeutic intervention. While advancing through the lesion, guide wire 100 may be moving in a direction away from a desired course, such as exiting the vessel wall rather than staying within the vessel lumen. Because guide wire 100 is being advanced in a lesion, it is resistant to steering attempts due to frictional forces the lesion imparts upon guide wire 100. In such a case, distal end 62 of catheter 10 is advanced to distal end 104 of guide wire 100. Catheter is then pressurized, causing distal tip 62 to deflect and helping to establish a new direction for advancing guide wire 100.

Figure 5:
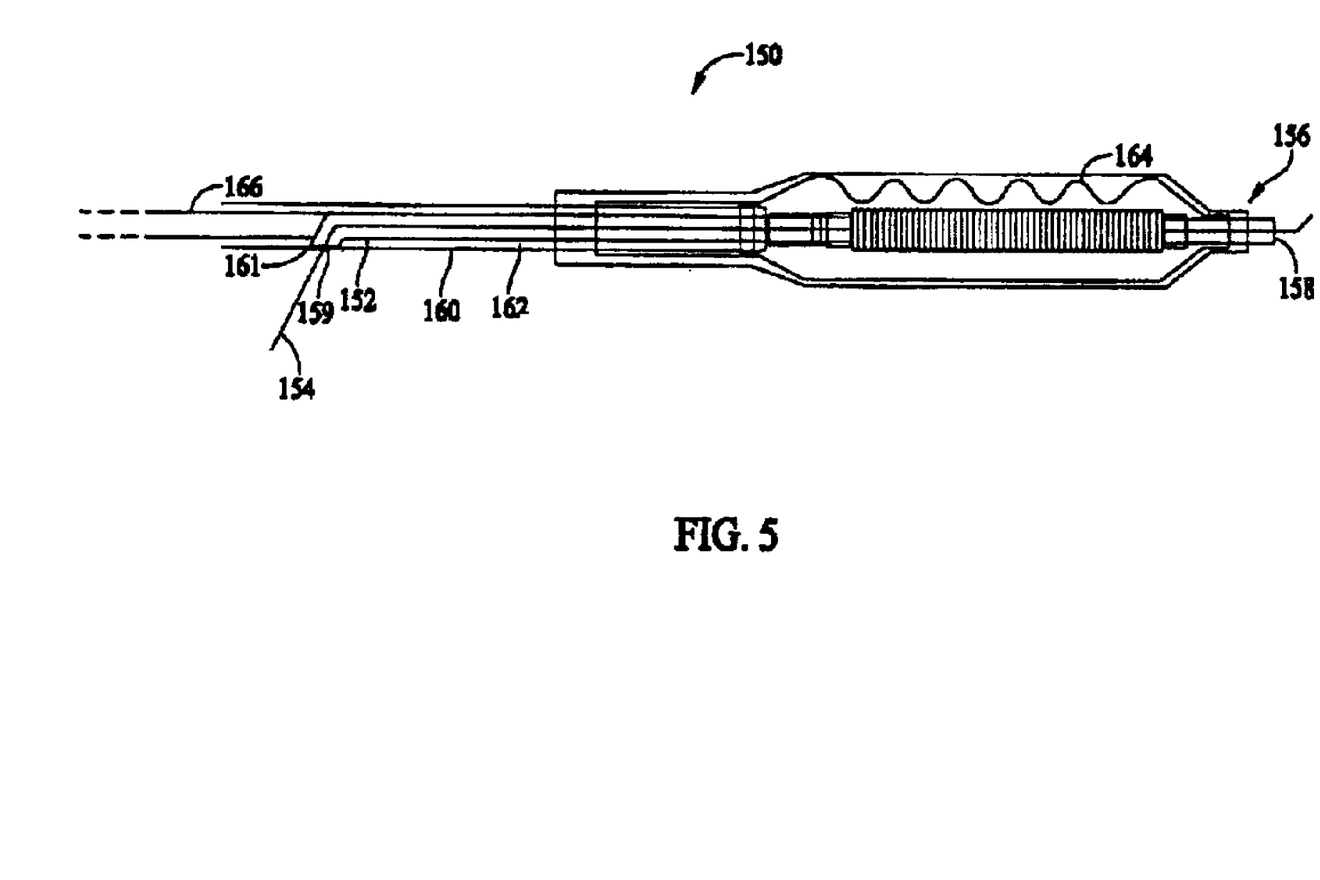
FIG. 5 is an illustration of a distal tip of a rapid exchange deflecting catheter in accordance with an alternative embodiment.

FIG. 5 illustrates a rapid exchange deflecting catheter 150. An inner tube 152 forms a guide wire lumen and is shortened compared to catheter 10 (shown in FIGS. 1–4). Guide wire 154 enters catheter 150, in one embodiment, approximately 30 cm from distal end 156 and exits a distal tip 158 of catheter 150. Inner tube 152 provides an exit opening 159 for guide wire 154 through an outer wall of outer tube 160. In one embodiment, exit opening 159 of inner tube 152 is positioned closer to distal tip 158 than a proximal end (not shown) of catheter 150 and is flush with outer tube 160. A junction 161 between inner tube 152 and outer tube 160 is sealed with a suitable adhesive to maintain a passageway 162 within outer tube 160 to deflecting balloon 164. A shaft 166, which in alternative embodiments is either solid or hollow core material extends from a LUER fitting (not shown) to inner tube 152. Shaft 166 is rigid enough to allow catheter 150 to be pushed or pulled along guide wire 154, but is also flexible enough to track along tortuous paths. Outer tube 160 is attached to a LUER fitting, as described above, thereby establishing an annulus conduit between shaft 166 and outer tube 160, thereby continuing through the conduit established between outer tube 160 and inner tube 152.

The rapid exchange embodiment of catheter 150 eliminates a need for a rotating hub assembly as described with respect to catheter 10 shown in FIGS. 1–4. A rapid exchange configuration allows catheter exchanges to be performed with guide wires that are shorter than twice the length of the catheter.

Embodiments of a low profile support catheter including a deflecting distal end to change the direction of a guide wire therein in situ has many potential uses within a body. The deflection of the catheter allows better selection of arteries, especially at bifurcations in tortuous anatomy. For example, selecting the circumflex coronary artery from a long left main coronary artery can be challenging with a guide wire alone, while a deflecting catheter assists a user by allowing additional bending of the wire's path. Saphenous vein grafts can also be very tortuous, especially at the anastomosis sites. Such a deflecting catheter provides a benefit to such a procedure as the guide wire can be steered. Alternately, a deflecting support catheter provides a benefit when a guide wire is traversing a long, tight stenosis or a total occlusion when the artery is totally blocked. The catheter supports the wire and causes the wire to be stiffer by its close coaxial placement. Such a deflection also helps overcome the resilience of any lesions, especially when the wire is advancing in an undesirable direction such as towards the arterial wall.

While the invention has been described in terms of various specific embodiments, those skilled in the art will recognize that the invention can be practiced with modification within the spirit and scope of the claims.

What is claimed is:

1. A catheter comprising:
    a distal end;
    a proximal end;
    an outer tube extending from said distal end to said proximal end; and
    an inner tube extending through a length of said outer tube, said proximal end comprising an inflation port, an inner hub bonded to said outer tube and forming a seal therewith, and a flexible tube extending between said inflation port and said inner hub, said outer tube and said inner hub configured to rotate with respect to said inflation port.

2. A catheter in accordance with claim 1 wherein said inner tube comprises:
    an inner layer configured to allow a guide wire to pass therethrough;
    a middle layer configured to keep said inner tube from collapsing when bent; and
    an outer layer configured to resist hydraulic pressure.

3. A catheter in accordance with claim 2 wherein said inner layer comprises at least one of polytetraflouroethylene, polyimide, and polyetheretherketone.

4. A catheter in accordance with claim 2 wherein said middle layer comprises a coil of flat stainless steel ribbon.

5. A catheter in accordance with claim 2 wherein said middle layer comprises a coil of metal.

6. A catheter in accordance with claim 2 wherein said outer layer has a thickness of about 0.0005 inch to about 0.001 inch.

7. A catheter in accordance with claim 2 wherein said outer layer comprises at least one of polytetraflouroethylene, polyimide, and polyetheretherketone.

8. A catheter in accordance with claim 1 wherein said inflation port is configured to be attached to a LUER fitting.

9. A catheter in accordance with claim 1 wherein said inner hub forms an annulus between said inner tube and said outer tube.

10. A catheter in accordance with claim 1 further comprising:
    an outer hub; and
    bushings rotatably connecting said inner hub to said outer hub.

11. A catheter in accordance with claim 10 wherein said inflation port extends from said outer hub.

12. A catheter in accordance with claim 1 wherein said distal end comprises a corrugated section attached to an end of said inner tube, and an asymmetric balloon attached to said outer shaft and fluidly coupled to said inflation port.

13. A catheter in accordance with claim 12 wherein said balloon comprises a curved inflated configuration such that inflation of said balloon causes a deflection of said distal end.

14. A catheter in accordance with claim 12 wherein a first side of said balloon comprises a greater length of balloon material than a second side of said balloon.

15. A catheter in accordance with claim 1 wherein said catheter comprises one of an over the wire catheter and a rapid exchange catheter.

16. A catheter in accordance with claim 15 wherein said outer tube comprises an outer wall and an exit opening extending through said outer wall, said inner tube extending from said exit opening.

17. A catheter in accordance with claim 16 wherein said exit opening is positioned closer to said catheter distal end than said catheter proximal end.

18. A catheter in accordance with claim 15 wherein said outer tube comprises an outer wall and an exit opening extending through said outer wall, said exit opening flush with an outer wall of said outer tube.

19. A catheter comprising:
    a distal end;
    a proximal end;
    an outer tube extending from said distal end to said proximal end; and
    an inner tube extending through said outer tube, said distal end comprising a corrugated section attached to an end of said inner tube, and an asymmetric balloon attached to said outer tube and configured to deflect said distal end of said catheter.

20. A catheter in accordance with claim 19 wherein said balloon comprises a curved configuration.

21. A catheter in accordance with claim 19 wherein said corrugated section is positioned with said balloon.

22. A catheter in accordance with claim 19 wherein said corrugated section is configured to withstand pressurization and comprises tubing that is more flexible than said inner tube.

23. A catheter in accordance with claim 19 wherein said corrugated section comprises corrugated polyethylene terephthalate (PET) heat shrink tubing.

24. A catheter in accordance with claim 19 wherein said distal end comprises a plurality of radiopaque marker bands, a respective said band attached to a respective end of said corrugated section.

25. A catheter in accordance with claim 19 further comprising a smoothing sleeve extending around said deflection balloon.

26. A catheter in accordance with claim 19 wherein said catheter comprises one of an over the wire catheter and a rapid exchange catheter.

27. A catheter in accordance with claim 26 wherein said outer tube comprises an outer wall and an exit opening extending through said outer wall, said inner tube extending from said exit opening.

28. A catheter in accordance with claim 26 wherein said exit opening is positioned closer to said catheter distal end than said catheter proximal end.

29. A catheter in accordance with claim 26 wherein said outer tube comprises an outer wall and an exit opening extending through said outer wall, said exit opening flush with an outer wall of said outer tube.

30. A method for deflecting a catheter, the catheter including a distal end, a proximal end, an outer tube extending from the distal end to the proximal end, and an inner tube extending through the outer tube, the proximal end including an inflation port, a rotating hub bonded to the outer shaft, a flexible tube extending between the inflation port and the rotating hub, the outer tube and inner tube rotatable with respect to the inflation port, the distal end including a corrugated section attached to an end of the inner passage tube, and a deflection balloon attached to the outer tube and configured to expand more on one side than another side, said method comprising:

provide a fluid at the inflation port;

pressurizing the fluid such that it passes through the inflation port, through the flexible tube, into the rotating hub, into a space between the inner tube and the outer tube, and into the deflecting balloon; and causing the balloon to inflate until a desired deflection of the distal end is achieved.

31. A method according to claim 30 further comprising rotating the catheter until the distal end extends in a desired direction of travel.

32. A method according to claim 30 wherein the distal end includes radiopaque marker bands at each end of the corrugated section, said method comprising monitoring a position of the marker bands; and determining a deflection of the distal end based on the position of the marker bands.

* * * * *